May 27, 1941. C. L. FITZGERALD Plant Pat. 467
ROSE
Filed Dec. 7, 1940
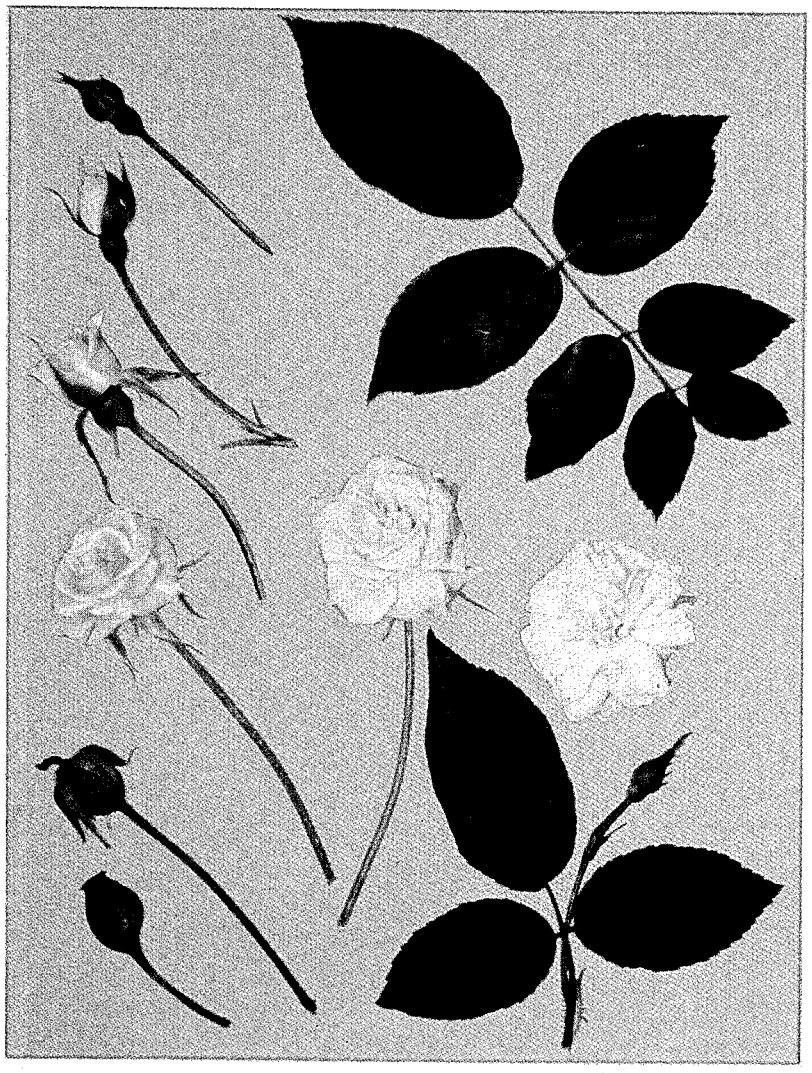
INVENTOR:
CHARLES L. FITZGERALD,
BY Alfred W. Knight
ATTORNEY Patented May 27, 1941

Plant Pat. 467

UNITED STATES PATENT OFFICE

467

ROSE

Charles L. Fitzgerald, Hawthorne, Calif.

Application December 7, 1940, Serial No. 369,086

1 Claim. (Cl. 47—61)

My invention relates to improvements in "baby" roses, and pertains particularly to a salmon-pink rose of a size comparable to the well-known Cecil Brunner, but differing therefrom in color of flower and in certain other particularities. The variety of rose of the present invention is the result of hybridization and cross-hybridization from hybrid highly colored roses of my own development, and the Cecil Brunner. These hybrid highly colored roses were developed between 1911 and 1926, and the small well colored roses from these plants were cross-bred with a bush Cecil Brunner as a mother. The well-developed crosses from this hybridization were then bred and cross-bred to and with a bush Cecil Brunner, with the realization of the present variety in 1934.

The parent seedling of the present variety was grown under glass until six inches tall, was transplanted and has since been growing outside, at a location near the City of Los Angeles, California, within a few miles of the Pacific Ocean and within the so-called "fog-belt." This variety has been found to reproduce asexually true to type and character.

The accompanying color plate shows the development of a bloom from an immature bud through the full-blown stage, together with an old wood leaf-branch of seven fingers and a new wood leaf-branch of three fingers.

The following is a detailed description of my new rose. Where references are made herein to colors, by plate and number, it will be understood that the reference is to the corresponding plate and color patch of "A Dictionary of Color" (Maerz and Paul, McGraw-Hill 1930). Where a color name is given in parentheses, following the plate and number, that name is the one ascribed by Maerz and Paul as being the most common name for such color.

The instant rose is a heavy bloomer, after the winter rest. Some buds and flowers remain on the bush throughout the rest of the year and often past the first of January following, depending upon the winter weather. The rose is of the type of the Cecil Brunner in general blooming habits, is strong and well rooted. It is very strongly resistant to mildew, rust, and black-spot. It is very fragrant.

*The plant*

The rose is a bush or upright rose, of vigorous growing habits. The foliage is abundant. The leaf is unequally pinnate, and when mature is comprised of seven leaflets, although leaves with five and nine leaflets occasionally occur. The mature leaf measures about four and one-half inches long and about three inches wide, as measured from tip-to-tip of the largest opposite leaflets. The leaflets are glossy in texture, are long and pointed with slightly irregular edge serrations spaced from one-sixteenth to three-thirty-seconds of an inch. The petiole is about two and one-quarter inches long, has two opposed adnate stipules, and carries, occasionally, some small briars on the underside. The leaf color approximates Plate 24, L—1 (Yew Green).

The color of new wood approximates Plate 7, L—6 (India Red) and the color of old wood approximates Plate 24, L—1 (Yew Green).

A few fair-sized thorns occur on old wood at the base or crown; on green wood the thorns are few and far between. The flower stems and small branches are almost free of thorns; some very small or fine prickles and some short needles occur on some leaf stems and on almost all flower stems. The color of the thorns when new approximates Plate 7, H—3 (Haematite Red).

*The flower*

The buds just prior to opening are ovoid, approximately seven-sixteenths inch in diameter and about three-quarters inch long from the tip of the sepals to the juncture of the calyx with the peduncle, which is stipulate. The color of the calyx approximates Plate 15, L—4 (Olive Green); the sepals being the same color with the edges approaching Plate 13, K—1, and with an overshading of Plate 13, K—12 (Gold Pheasant). The sepals darken slightly as the bud becomes more mature.

The color of the bud petals shade from Plate 2, K—8 (Begonia Gaiety—) to Plate 9, K—5 (Apricot Yellow) at the base. The peduncle approximates Plate 15, L—4 (Olive Green) in color, with a shading of Plate 15, J—9.

Upon opening, the bloom is suggestive of the well-known "Talisman" rose, the flower petals being of a color approximating Plate 2, I—3 (Jasper Pink); when about half open, the color of the petals is that of Plate 2, G—10 (Baby Rose); when about three-quarters open the color is that of Plate 2, C—9 (Rose Caroline) with the outer portions of the leaf retaining a pinker cast as a general rule, approximating Plate 2, J—4 (Camellia). When the bloom is full open, the petals roll back, and the principal coloring of the petals is approximately that of Plate 2, E—2. As the bloom matures, the deep yellow coloring (Plate 9, K—5) of the base portions gradually fades, approaching a color approximating Plate 9, K—3 (Empire Yellow) to Plate 9, K—1.

The petals also exhibit a veining of deeper pink as intense as Plate 1, D—5 to a somewhat lighter color, such as Plate 1, E—3. The permanence of the bloom is good, the petals adhering quite well. The petalage is double, arranged in six rows. The full open form of the bloom is globular. The bloom is distinctly fragrant. Furthermore, the above colors were determined upon flowers growing on bushes planted outside, late in August, and if the buds are picked for a bouquet and kept inside, the colors remain a deeper shade.

*Genital organ*

The general form, size and shape of the various organs are comparable to those found in a rose of the size of this particular rose. The color of the stamens is substantially that of Plate 10, L—1; the color of the anthers is that of Plate 10, L—6 (Ta-Ming); the color of the pollen is that of Plate 10, L—9; the color of the styles is that of Plate 6, L—8 (Dark Cardinal); the color of the stigmas is that of Plate 11, J—6 (Honeysweet); and the color of the ovaries is that of Plate 11, B—1 (New Silver+). This rose does not seed itself. Only seldom does one find seeds in the fruit, and then but one or two.

*Fruit*

The fruit is about three-quarters of an inch in length at maturity, and about one-half inch in diameter; ovoid. Usually sterile unless the bloom was hand fertilized. The sepals dry up before the fruit matures, and drop or are blown off by the wind. The color of the mature fruit approximates Plate 7, L—7 (Maroon).

I claim:

The variety of fragrant hybrid baby rose herein shown and described, characterized particularly in its salmon-pink coloring, its vigorous growth and blooming habits, relative freedom from thorns, and its resistance to mildew, rust and black spot.

CHARLES L. FITZGERALD.